(12) United States Patent
Tian et al.

(10) Patent No.: US 12,070,614 B2
(45) Date of Patent: Aug. 27, 2024

(54) APPARATUS AND METHOD FOR MAGNETIC PARTICLE IMAGING AND THERMOTHERAPY FUSION BASED ON FIELD-FREE LINE INERTIAL SCANNING

(71) Applicant: BEIHANG UNIVERSITY, Beijing (CN)

(72) Inventors: Jie Tian, Beijing (CN); Jie He, Beijing (CN); Hui Hui, Beijing (CN); Jing Zhong, Beijing (CN); Yu An, Beijing (CN); Zhenchao Tang, Beijing (CN)

(73) Assignee: Beihang University (CN)

( * ) Notice: Subject to any disclaimer, the term of this patent is extended or adjusted under 35 U.S.C. 154(b) by 78 days.

(21) Appl. No.: 18/115,888

(22) Filed: Mar. 1, 2023

(65) Prior Publication Data

US 2023/0338740 A1    Oct. 26, 2023

(51) Int. Cl.
*A61N 1/40* (2006.01)
*A61B 5/0515* (2021.01)
*A61N 2/02* (2006.01)

(52) U.S. Cl.
CPC ............ *A61N 1/406* (2013.01); *A61B 5/0515* (2013.01); *A61N 2/02* (2013.01)

(58) Field of Classification Search
CPC ......... A61N 1/406; A61N 2/02; A61B 5/0515
See application file for complete search history.

(56) References Cited

U.S. PATENT DOCUMENTS

| 2011/0115487 | A1* | 5/2011 | Grodzki ................ | A61B 5/055 324/309 |
| 2012/0265050 | A1* | 10/2012 | Wang .................... | A61B 6/485 600/407 |
| 2016/0223626 | A1* | 8/2016 | Schmale ................. | H01F 7/20 |

* cited by examiner

*Primary Examiner* — Christine H Matthews
*Assistant Examiner* — Joshua Daryl D Lannu (57) ABSTRACT

An apparatus and a method for magnetic particle imaging and thermotherapy fusion based on field-free line inertial scanning comprises a magnetic body group, an induction coil, a living body bed, a control device, a display device, an image processing device and a cooling system. The magnetic body group comprises a long curved magnetic body pair and a cylindrical magnetic body. The control device is used to scan and image the target living body and perform thermotherapy on a preset area.

8 Claims, 5 Drawing Sheets

APPARATUS AND METHOD FOR MAGNETIC PARTICLE IMAGING AND THERMOTHERAPY FUSION BASED ON FIELD-FREE LINE INERTIAL SCANNING

TECHNICAL FIELD

This invention generally relates to the technical field of magnetic particle imaging and thermotherapy fusion, and more particularly, to an apparatus and a method for magnetic particle imaging and thermotherapy fusion based on field-free line inertial scanning.

BACKGROUND

In magnetofluid thermotherapy, by adopting a suspension liquid of magnetic nanoparticles to achieve a whole or local dosing while combining with an alternating magnetic field imposed externally, heat is generated through a process called induction to ablate target tissues. Heat generated when the temperature is higher than a mammalian body temperature (37° C.) may induce apoptosis and/or enhance the sensitivity of the target tissues to other therapies, such as radiotherapy and chemotherapy. While most of the thermotherapy techniques currently under development aim at cancer treatment, thermotherapy can also be used to treat restenosis, remove plaque, ablate ganglion and alleviate pain by increasing local blood flow. Although magnetofluid thermotherapy may be invasively performed to a treated area, it is challenging to non-invasively locate a treated area by induction.

In recent years, magnetic particle imaging (MPI), a new imaging method based on superparamagnetic iron oxide nanoparticles (SPIONs), has been proposed. This technology utilizes the non-linearity response and re-magnetization of magnetic nanoparticles in the field-free space of a high gradient magnetic field to sensitively and quantitatively obtain a three-dimensional concentration distribution of magnetic nanoparticles in a living body. Because the specific absorption rate (SAR) in the distribution area of magnetic nanoparticles is in direct proportion to the concentration of magnetic nanoparticles, the three-dimensional specific absorption rate (SAR) distribution in the living body is obtained simultaneously. Meanwhile, the temperature image of the distribution area of magnetic nanoparticles is obtained by utilizing the relaxation effect of magnetic nanoparticles or the sensitivity of spectral characteristics to ambient temperature. The aforesaid properties of magnetic particle imaging (MPI) allow the thermal dosing to be precisely set and the non-invasive real-time temperature monitoring of magnetofluid thermotherapy to be realized.

Presently, magnetic particle imaging (MPI) achieves image reconstruction based on constructing a field-free region (FFR), namely, a field-free point (FFP) or a field-free line (FFL), receiving the magnetization response signals of magnetic nanoparticles in the field-free region by highly sensitive coils, and encoding the scanning trace of the field-free region. Compared with the field-free point scanning imaging, the temporal-spatial resolution and sensitivity of the field-free line scanning imaging are significantly improved. In the field-free line scanning imaging, radio frequency excitation is continuously imposed on magnetic nanoparticles in the field-free region. Due to the relaxation effect, magnetic nanoparticles release heat to the ambient environment, while magnetic nanoparticles outside the field-free region are in a saturated state such that they do not release heat to the ambient environment. This magnetic field property of magnetic particle imaging (MPI) equipment allows magnetofluid thermotherapy to be precisely positioned. Assume that the field-free line rotates around the preset area for thermotherapy and the rotation center of the field-free line is the preset area for thermotherapy, the preset area is always in the field-free region such that it can be heated continuously. However, magnetic nanoparticles far away from the preset area for thermotherapy stay in the field-free region for a short time, which avoids magnetic heat from being obviously generated such that a precise positioning of field-free line thermotherapy is achieved.

A classic three-dimensional field-free line electric scanning MPI equipment includes at least five Maxwell coil pairs and three-dimensional scanning coils, resulting in complex structure and difficult control. Compared with it, a long curved magnetic body pair is capable of generating and translating a field-free line gradient magnetic field, and a three-dimensional field-free line scanning can be realized by matching the mechanical rotation of the long curved magnetic body pair and the translation of the living body bed, which greatly reduces the difficulty of the control and structural design of MPI equipment. In conclusion, to overcome the shortcomings of conventional magnetofluid therapies in image-guided treatment, precise setting of thermal dosing, non-invasive real-time temperature monitoring and accurate positioning, and to simplify the structure and control of the field-free line scanning MPI equipment, the present invention provides an apparatus and a method for magnetic particle imaging and thermotherapy fusion based on field-free line inertial scanning.

SUMMARY

To solve the technical problems in prior art, namely, technical problems relating to the lack of image-guided treatment, precise setting of thermal dosing, non-invasive real-time temperature monitoring and accurate positioning, as well as the high complexity of designing the structure and control of classic field-free line scanning MPI equipment. The purpose of the present invention is to provide an apparatus for magnetic particle imaging and thermotherapy fusion based on field-free line inertial scanning, comprising: a magnetic body group, an induction coil, a living body bed, a control device, a display device, an image processing device and a cooling system.

To achieve the above purpose, the present invention adopts the following technical solution:

The magnetic body group comprises a long curved magnetic body pair and a cylindrical magnetic body. A long curved magnetic body in the long curved magnetic body pair comprises a first structural member, a second structural member and a third structural member. The first structural member and the third structural member are U-shaped magnetic bodies. The second structural member comprises two symmetrical arc-shaped magnetic bodies prepared using a preset curvature. The first structural member is parallel to the third structural member, and a plane where the second structural member is located is perpendicular to a plane where the first structural member is located. The two ends of the second structural member are respectively connected to the open ends of the U-shaped magnetic bodies of the first structural member and the third structural member.

The long curved magnetic bodies of the long curved magnetic body pair are of the same shape. The long curved magnetic bodies are parallel to each other, and their central axes are collinear. The closed ends of the first structural member or the third structural member of the long curved magnetic bodies of the long curved magnetic body pair are arranged oppositely.

The cylindrical magnetic body is arranged in a space surrounded by the long curved magnetic body pair, and the axis of the cylindrical magnetic body is perpendicular to the central axis of the long curved magnetic body pair.

The current component in the same direction and the current component in the reverse direction may be simultaneously introduced into the long curved magnetic body pair for generating and translating the field-free line. Though changing the current component in the same direction, the biasing position of the field-free line is adjusted, and through changing the current component in the reverse direction, the gradient of the gradient magnetic field is adjusted.

A direct current component and a radiofrequency current component may be introduced into the cylindrical magnetic body. The direct current component introduced into the cylindrical magnetic body is used for adjusting the depth of the field-free line in the axial direction of the cylindrical magnetic body, and the radio frequency current component introduced into the cylindrical magnetic body is used for the induction heating of magnetic nanoparticles in the field-free region.

There are two groups of induction coils, which are curved rectangular coils closely attached to the cylindrical magnetic body, wherein one group of induction coils is arranged on the inner wall of the cylindrical magnetic body, and the other group of induction coils is arranged on the outer wall of the cylindrical magnetic body. The central axes of the two groups of curved rectangular coils are perpendicular to each other.

The control device is used to control the current variation and mechanical rotation of the long curved magnetic body pair, control the current variation of the cylindrical magnetic body, control the moving depth of the living body bed, and control the hydraulic pressure of the cooling system according to the preset control command, thereby realizing the translation, rotation and serial-layer scanning of the generated field-free line. Therefore, the scanning and imaging of the target living body and the positioning of the field-free line are realized, allowing thermotherapy to be performed on a preset area of the target living body.

The cooling system is used to absorb the heat generated by the apparatus for magnetic particle imaging and thermotherapy fusion based on field-free line inertial scanning when performing the thermotherapy using a hollow core conductor.

In another preferred embodiment of the present invention, the apparatus for magnetic particle imaging and thermotherapy fusion based on field-free line inertial scanning performs three-dimensional scanning and positioning thermotherapy by taking the axial direction of the cylindrical magnetic body as they direction and the axial direction of the cylindrical coil as the z direction.

In another preferred embodiment of the present invention, when realizing the positioning of the field-free line and performing thermotherapy on a preset area of the target living body, the induction coil is in an off state.

A method for magnetic particle imaging and thermotherapy fusion based on field-free line inertial scanning, comprising the steps of:

Step 100: constructing a gradient magnetic field based on the long curved magnetic body pair and forming a field-free line;

Step 200: controlling the field-free line to translationally rotate in a plane perpendicular to the axis of the cylindrical magnetic body, and performing tomographic scanning on a target living body on the living body bed to obtain electromagnetic induction signals; subsequently, preprocessing the electromagnetic induction signals to obtain a tomographic image group;

Step 300: controlling a living body bed or a field-free line to move along the axis direction of the cylindrical magnetic body to a preset depth, and serial-layer-scanning the target living body on the living body bed to obtain a complete tomographic image group;

Step 400: classifying and fusing the complete tomographic image group to obtain a three-dimensional image group;

Step 500: determining a thermotherapeutic program according to the three-dimensional image group, wherein the thermotherapeutic program includes the areas to be treated, the sequence of areas to be treated, the duration of thermotherapy and the size of areas to be treated;

Step 600: constructing a gradient magnetic field based on the long curved magnetic body pair and forming a field-free line;

Step 700: controlling the field-free line to rotate around the area to be treated and controlling the cylindrical magnetic body to generate a radio frequency magnetic field according to the thermotherapeutic program, thereby performing thermotherapy on the area to be treated;

Step 800: repeatedly switching between the imaging mode and the thermotherapy mode until the thermotherapeutic program is completed, wherein the imaging mode includes steps 100, 200 and 300, and the thermotherapy mode includes steps 600 and 700.

In another preferred embodiment of the present invention, the tomographic image group includes a concentration distribution tomographic image of the magnetic nanoparticles, a temperature tomographic image of the distribution area, and an SAR (specific absorption rate) tomographic image of the distribution area. The three-dimensional image group includes a three-dimensional image of the concentration of magnetic nanoparticles, a three-dimensional image of the temperature of the distribution area, and a three-dimensional image of the SAR (specific absorption rate) of the distribution area.

In another preferred embodiment of the present invention, controlling the field-free line to translate and rotate in a plane perpendicular to the axis of the cylindrical magnetic body, comprising: controlling the same-directional current component of the long curved magnetic body pair, thereby enabling the field-free line to translate and reciprocate along the central axis direction of the long curved magnetic body pair while controlling the long curved magnetic body pair to mechanically rotate in a reciprocating manner around the axis of the cylindrical magnetic body.

In another preferred embodiment of the present invention, controlling the living body bed or field-free line to move along the axis direction of cylindrical magnetic body to a given depth, thereby serial-layer-scanning the target living body on the living body bed, comprising: controlling the living body bed to deliver the target living body to a preset position in the cylindrical magnetic body, or controlling the current of the cylindrical magnetic body to make the field-free line to move along the axis direction of the cylindrical magnetic body to a preset depth; meanwhile, controlling the field-free line to perform translational rotation to form a serial-layer scanning, and the scanning surface is a plane formed by an axis perpendicular to the cylindrical magnetic body.

In another preferred embodiment of the present invention, controlling the field-free line to rotate around the area to be treated, comprising:

Controlling the current of the long curved magnetic body pair, translating the long curved magnetic body pair to a preset position on a plane perpendicular to the axis of the cylindrical magnetic body, and controlling the long curved magnetic body pair to mechanically rotate around the axis of the cylindrical magnetic body to a specified angle, thereby enabling the center point of the field-free line, namely, the projection position of the area to be treated, to stay on the plane perpendicular to the axis of the cylindrical magnetic body;

Subsequently, controlling the living body bed by the control device, and delivering the area of the target living body to be treated to the plane formed by the central axis of the long curved magnetic body pair, or controlling the direct current component of the cylindrical magnetic body, and moving the field-free line along the axis direction of the cylindrical magnetic body to the area to be treated;

Finally, controlling the long curved magnetic body pair to mechanically rotate in a reciprocating manner around the central axis of the long curved magnetic body pair.

In another preferred embodiment of the present invention, adjusting the thermotherapeutic area of the apparatus for magnetic particle imaging and thermotherapy fusion based on field-free line inertial scanning is to control the current component in reverse direction of the two long curved magnetic body pairs.

In another preferred embodiment of the present invention, preprocessing the electromagnetic induction signals includes denoising and filtering amplification.

Compared with the prior art, the present invention has the following advantages:

The present invention realizes a magnetic fluid hyperthermia with image-guided treatment, precise setting of thermal dosing, non-invasive real-time temperature monitoring and accurate positioning while simplifying the structure and control of the apparatus of the present invention; through adopting the present invention, the temporal-spatial resolution and sensitivity of the imaging are significantly improved and no longer limited by tissue depth, and the positioning effect and range of thermotherapy are effectively controlled;

The invention has two operating modes: imaging and thermotherapy. In the imaging mode, by controlling the introduced current and mechanical rotation of the magnetic body group as well as the movement of the living body bed, the field-free line scanning tomographic image group and three-dimensional image group based on magnetic nanoparticles are obtained. Based on the three-dimensional image group, a thermotherapeutic program is determined. In the thermotherapy mode, by controlling the introduced current and mechanical rotation of the magnetic body group as well as the movement of the living body bed, the field-free line local quantitative thermotherapy based on magnetic nanoparticles is realized. The imaging mode and thermotherapy mode are repeatedly switched until the desired thermotherapeutic goal is achieved. The present invention provides a novel magnetofluid thermotherapy, which includes the therapeutic plan, therapeutic monitoring and local space induction heating.

BRIEF DESCRIPTION OF THE DRAWINGS

By referring to the drawings and the detailed description of the embodiments, other features, purposes and advantages of the present invention become clearer.

FIG. 3 is a schematic diagram illustrating a three-dimensional structure of one long curved magnetic body pair and a two-dimensional contour map of the magnetic flux density generated by the long curved magnetic body pair in an embodiment of the present invention; wherein FIG. 3(a) is a schematic diagram illustrating a physical structure of the long curved magnetic body pair, FIG. 3(b) is a schematic diagram illustrating the contour lines and gradient directions of the magnetic flux density in the xy plane, FIG. 3(c) is a schematic diagram illustrating the contour lines and gradient directions of the magnetic flux density in the yz plane, FIG. 3(d) is a schematic diagram illustrating the contour lines and gradient directions of the magnetic flux density in the zx plane;

FIG. 6 is a schematic diagram illustrating a structure of a computer system suitable for an electronic device in an embodiment of the present invention.

DETAILED DESCRIPTION

While specific embodiments of the invention have been described in detail, it will be appreciated by those skilled in the art that various modifications and alternatives to those details could be developed in light of the overall teachings of the invention. Accordingly, the particular arrangements disclosed are meant to be illustrative only and not limiting as to the scope of the invention which is to be given the full breadth of the claims appended and any and all equivalents thereof.

The present invention is further elaborated below in combination with drawings and embodiments. It should be understood that the specific embodiments described herein are merely used for illustrative purpose. It is worth mentioning that the embodiments and the features in the embodiments of the invention may be combined when there is no conflict.

An apparatus for magnetic particle imaging and thermotherapy fusion based on field-free line inertial scanning in embodiment 1 of the present invention comprises a magnetic body group, an induction coil, a living body bed, a control device, a display device, an image processing device and a cooling system.

The magnetic body group comprises a long curved magnetic body pair and a cylindrical magnetic body. A long curved magnetic body in the long curved magnetic body pair comprises a first structural member, a second structural member and a third structural member. The first structural member and the third structural member are U-shaped magnetic bodies. The second structural member comprises two symmetrical arc-shaped magnetic bodies prepared using a preset curvature. The first structural member is parallel to the third structural member, and a plane where the second structural member is located is perpendicular to a plane where the first structural member is located. The two ends of the second structural member are respectively connected to the open ends of the U-shaped magnetic bodies of the first structural member and the third structural member.

The long curved magnetic bodies of the long curved magnetic body pair are of the same shape. The long curved magnetic bodies are parallel to each other, and their central axes are collinear. The closed ends of the first structural member or the third structural member of the long curved magnetic bodies of the long curved magnetic body pair are arranged oppositely.

The cylindrical magnetic body is arranged in a space surrounded by the long curved magnetic body pair, and the axis of the cylindrical magnetic body is perpendicular to the central axis of the long curved magnetic body pair.

The current component in the same direction and the current component in the reverse direction may be simultaneously introduced into the long curved magnetic body pair for generating and translating the field-free line. Though changing the current component in the same direction, the biasing position of the field-free line is adjusted, and through changing the current component in the reverse direction, the gradient of the gradient magnetic field is adjusted.

A direct current component and a radiofrequency current component may be introduced into the cylindrical magnetic body. The direct current component introduced into the cylindrical magnetic body is used for adjusting the depth of the field-free line in the axial direction of the cylindrical magnetic body, and the radio frequency current component introduced into the cylindrical magnetic body is used for the induction heating of magnetic nanoparticles in the field-free region.

There are two groups of induction coils, which are curved rectangular coils closely attached to the cylindrical magnetic body, wherein one group of induction coils is arranged on the inner wall of the cylindrical magnetic body, and the other group of induction coils is arranged on the outer wall of the cylindrical magnetic body. The central axes of the two groups of curved rectangular coils are perpendicular to each other.

The control device is used to control the current variation and mechanical rotation of the long curved magnetic body pair, control the current variation of the cylindrical magnetic body, control the moving depth of the living body bed, and control the hydraulic pressure of the cooling system according to the preset control command, thereby realizing the translation, rotation and serial-layer scanning of the generated field-free line. Therefore, the scanning and imaging of the target living body and the positioning of the field-free line are realized, allowing thermotherapy to be performed on a preset area of the target living body.

The cooling system is used to absorb the heat generated by the apparatus for magnetic particle imaging and thermotherapy fusion based on field-free line inertial scanning when performing the thermotherapy using a hollow core conductor.

To clearly describe the apparatus for magnetic particle imaging and thermotherapy fusion based on field-free line inertial scanning of the present invention, drawings are combined hereinafter to elaborate the modules of the apparatus in an embodiment of the present invention.

Figure 1:
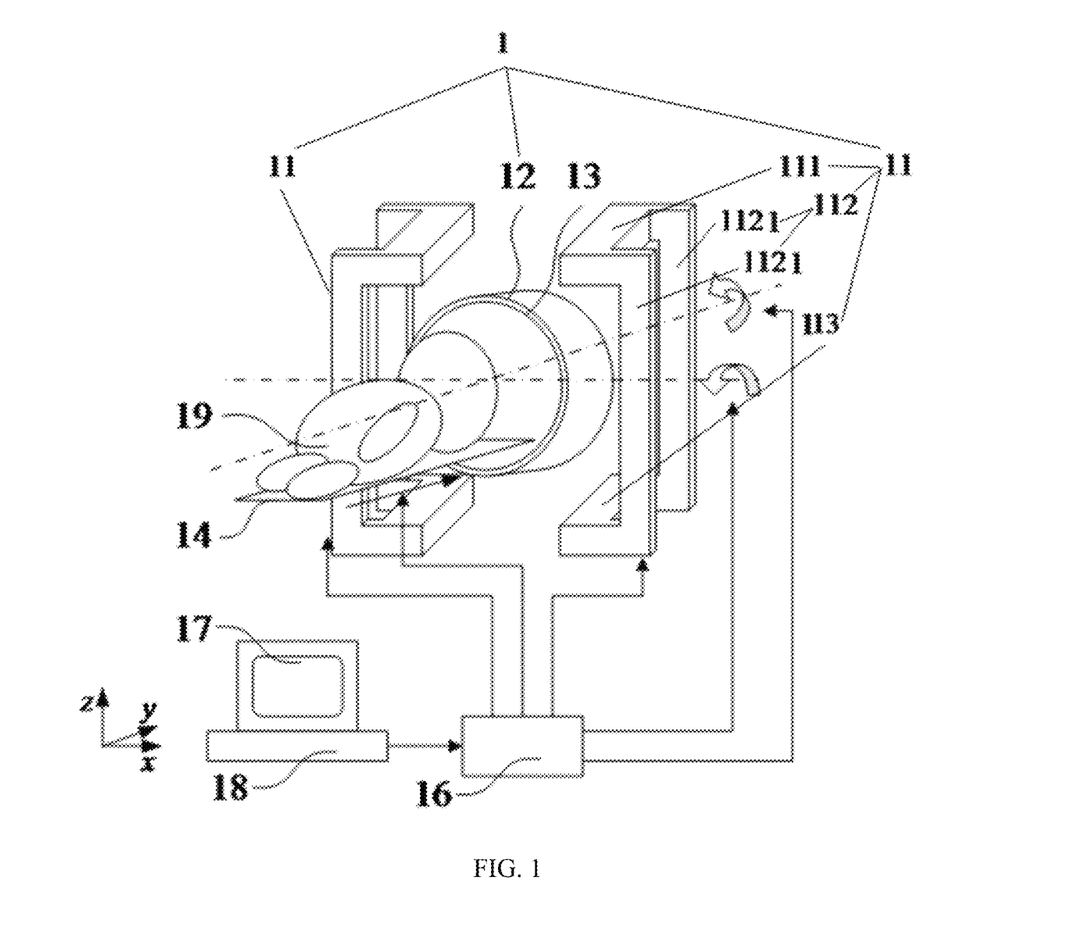
FIG. 1 is a schematic diagram illustrating a framework of the apparatus for magnetic particle imaging and thermotherapy fusion based on field-free line inertial scanning in an embodiment of the present invention.

As shown in FIG. 1, the apparatus for magnetic particle imaging and thermotherapy fusion based on field-free line inertial scanning comprises a magnetic body group 1 for generating a gradient magnetic field, an induction coil 13, a living body bed 14, a control device 16, a display device 17, an image processing device 18 and a cooling system, wherein the magnetic body group comprises a long curved magnetic body pair 11 and a cylindrical magnetic body 12.

Each long curved magnetic body in the long curved magnetic body pair comprises a first structural member 111, a second structural member 112 and a third structural member 113. The first structural member 111 and the third structural member 113 are U-shaped magnetic bodies. The second structural member 112 comprises two symmetrical arc-shaped magnetic bodies 1121 prepared using a preset curvature. The first structural member 111 is parallel to the third structural member 113, and a plane where the second structural member 112 is located is perpendicular to a plane where the first structural member 111 is located. The two ends of the second structural member 112 are respectively connected to the open ends of the U-shaped magnetic bodies of the first structural member 111 and the third structural member 113.

The long curved magnetic bodies of the long curved magnetic body pair are of the same shape. The long curved magnetic bodies are parallel to each other, and the central axes of the long curved magnetic bodies are collinear. The closed ends (namely, the bottoms of the U-shaped magnetic bodies) of the first structural member 111 or the third structural member 113 of the long curved magnetic bodies of the long curved magnetic body pair are arranged oppositely. As shown in FIG. 1, through adjusting the distance between the planes where the U-shaped magnetic bodies are located and the curvature of the arc-shaped magnetic bodies, the linearity of the gradient magnetic field of field-free line is significantly improved.

The current component in the same direction and the current component in the reverse direction may be simultaneously introduced into the long curved magnetic body pair for generating and translating the field-free line. Though changing the current component in the same direction, the biasing position of the field-free line is adjusted, and through changing the current component in the reverse direction, the gradient of the gradient magnetic field is adjusted. The control device is capable of controlling the long curved magnetic body pairs to respectively mechanically rotate in a reciprocating manner around the axis of the cylindrical magnetic body and the central axis of one group of the long curved magnetic body pairs.

Figure 3:
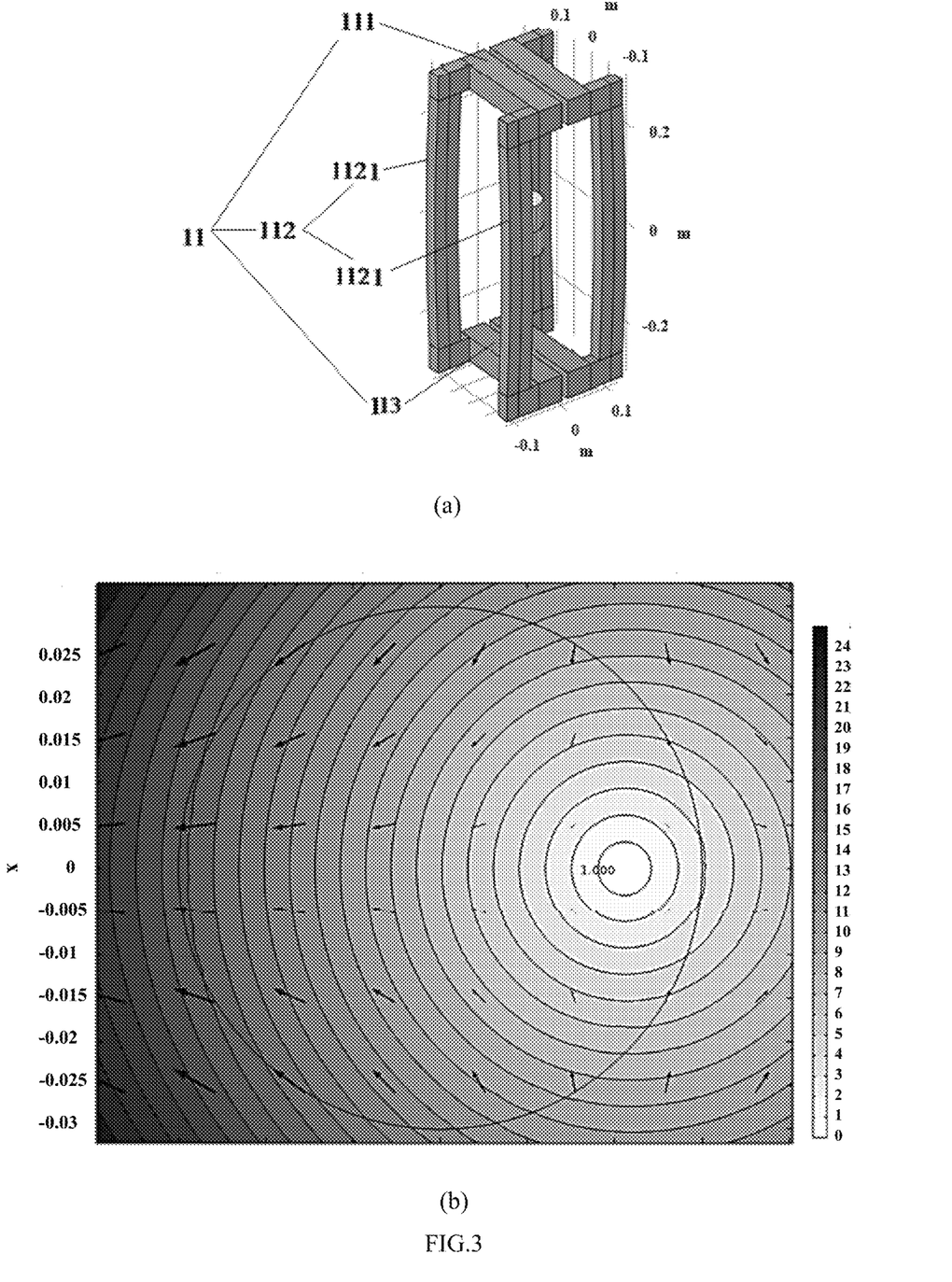

The long curved magnetic body pair of the present invention is mainly used to solve the problem relating to the low efficiency of field-free line gradient magnetic field generated by classical toroidal (Maxwell) magnet pairs (two groups of orthogonal Maxwell coil pairs are required to generate a field-free line gradient magnetic field) and the poor linearity of field-free line gradient magnetic field generated by classical "runway-shaped magnetic body pairs" (with semicircles on both sides and parallel and equal connecting lines in the middle). Through simulation research, the linearity of the field-free line gradient magnetic field generated by the long curved magnetic body pair is significantly improved. FIG. 3(a) shows a physical structure of the long curved magnetic body pair, wherein the cylinder in the middle is an FOV (Field of View). FIGS. 3(b)-(d) respectively show the contour lines and gradient directions of the magnetic flux density in the xy plane, yz plane and zx plane. At this point, the current component of the same strength in the same direction and the current component of the same strength in the reverse direction are simultaneously introduced into the long curved magnetic body pair. It can be seen from the current state and distance between the contour lines that the field-free line gradient magnetic field has a sufficiently high linearity. In FIGS. 3(b)-(d), the arrow direction represents a direction of current component, and the length of the arrow represents the strength of the current component.

The cylindrical magnetic body 12 is arranged in a space surrounded by the long curved magnetic body pair, and the axis of the cylindrical magnetic body is perpendicular to the central axis of the long curved magnetic body pair.

A direct current component and a radiofrequency current component may be introduced into the cylindrical magnetic body. The direct current component introduced into the cylindrical magnetic body is used for adjusting the depth of the field-free line in the axial direction of the cylindrical magnetic body, and the radio frequency current component introduced into the cylindrical magnetic body is used for the induction heating of magnetic nanoparticles in the field-free region.

The magnetic body group is used to construct and move the gradient magnetic field, as well as the field-free line generated accordingly, thereby saturating all magnetic nanoparticles outside the field-free line (the function of the gradient/scanning coil). Moreover, the magnetic body group is also used to construct a uniform magnetic field in an imaging mode, which enables the field-free line to move along the axis direction of the excitation coil to a given depth while constructing a radio frequency magnetic field in a thermotherapy mode. Therefore, the magnetocaloric effect of magnetic nanoparticles located at field-free points (the function of the excitation coil) is stimulated. The imaging mode and thermotherapy mode are described in detail below.

There are two groups of induction coils 13, which are curved rectangular coils closely attached to the cylindrical magnetic body, wherein one group of induction coils 13 is arranged on the inner wall of the cylindrical magnetic body, and the other group of induction coils 13 is arranged on the outer wall of the cylindrical magnetic body. The central axes of the two groups of curved rectangular coils are perpendicular to each other. In the imaging mode, the induction coils 13 collect the nonlinear response signals of magnetic nanoparticles, and in the thermotherapy mode, the induction coils 13 always keep an open-circuit state to avoid receiving signals with excessively high intensity caused by the coupling of the excitation module. The unfolded surface of the curved rectangular coil is rectangular.

The living body bed 14 is used to deliver the target living body to a given depth along the axis direction of the excitation coil. Preferably, a three-axis mechanical arm or a mechanical arm capable of moving freely in three directions under the control of a motor is adopted.

The cooling system is used to absorb the heat generated by the apparatus for magnetic particle imaging and thermotherapy fusion based on field-free line inertial scanning when performing thermotherapy using a hollow core conductor. Namely, the cooling system is used to take away the heat generated by the gradient/scanning coil (the long curved magnetic body) and the excitation coil (the cylindrical magnetic body) operating for a prolonged period in the thermotherapy mode.

The control device 16 is used to control the current variation and mechanical rotation of the long curved magnetic body pair, control the current variation of the cylindrical magnetic body, control the moving depth of the living body bed 14, and control the hydraulic pressure of the cooling system according to the preset control command, thereby realizing the translation, rotation and serial-layer scanning of the generated field-free line. Therefore, the scanning and imaging of the target living body 19 and the positioning of the field-free line are realized, allowing thermotherapy to be performed on a preset area (namely, the area to be thermally treated) of the target living body 19.

To perform thermotherapy on a preset area of a target living body 19 by realizing the positioning of the field-free line is to perform locally quantitative thermotherapy on diseased tissues according to the results of concentration imaging, temperature imaging and specific absorption rate (SAR) imaging of magnetic nanoparticles.

The image processing device 18 is used to process images obtained from the concentration imaging, temperature imaging and specific absorption rate (SAR) imaging of magnetic nanoparticles.

The display device 17 is used to display images processed by the image processing device 18.

In addition, the apparatus for magnetic particle imaging and thermotherapy fusion based on field-free line inertial scanning performs three-dimensional scanning and positioning thermotherapy by taking the axial direction of the cylindrical magnetic body as the y direction and the axial direction of the cylindrical coil as the z direction.

Figure 2:
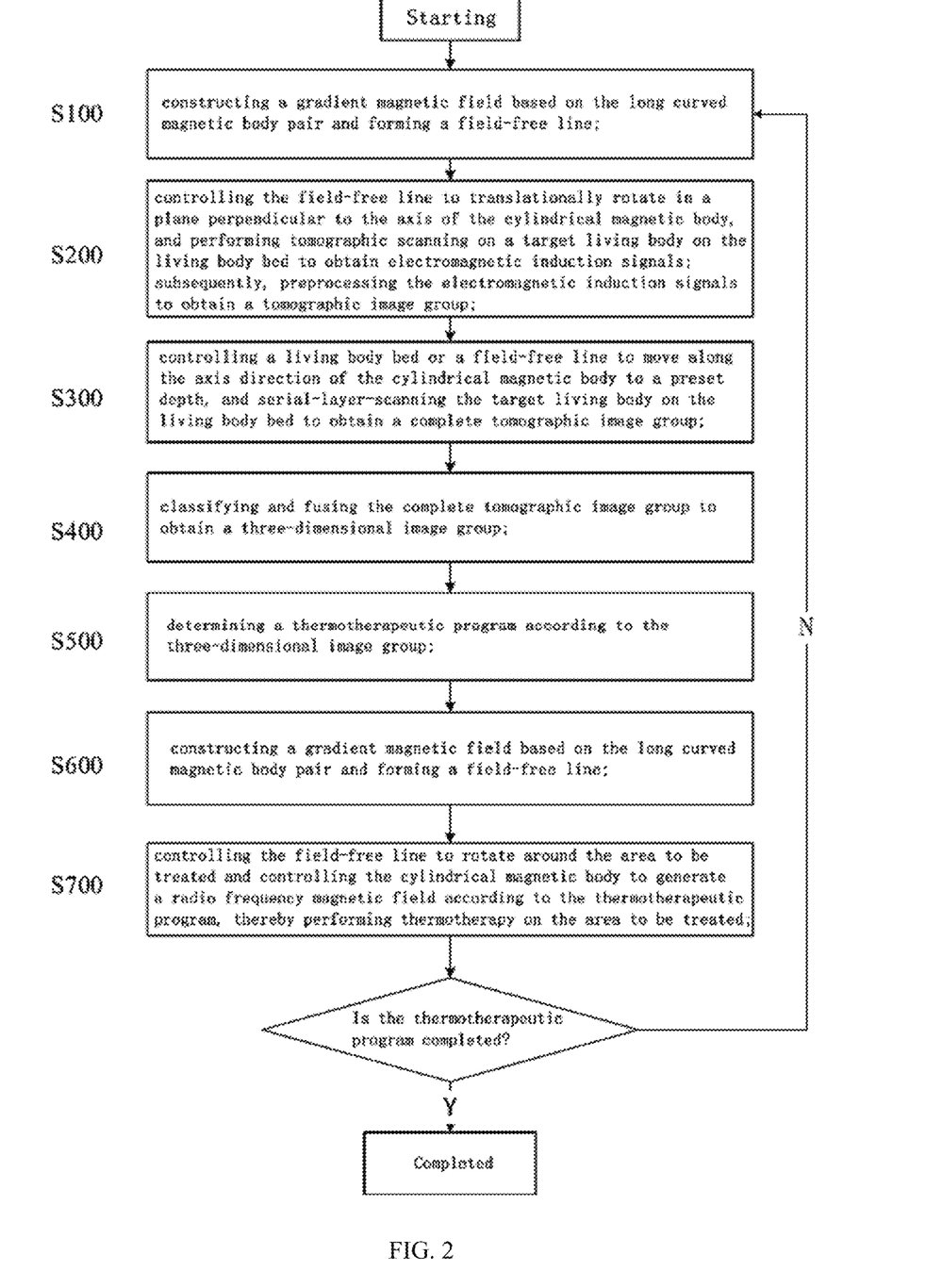
FIG. 2 is a flow chart illustrating the method for magnetic particle imaging and thermotherapy fusion based on field-free line inertial scanning in an embodiment of the present invention.
Figure 5:
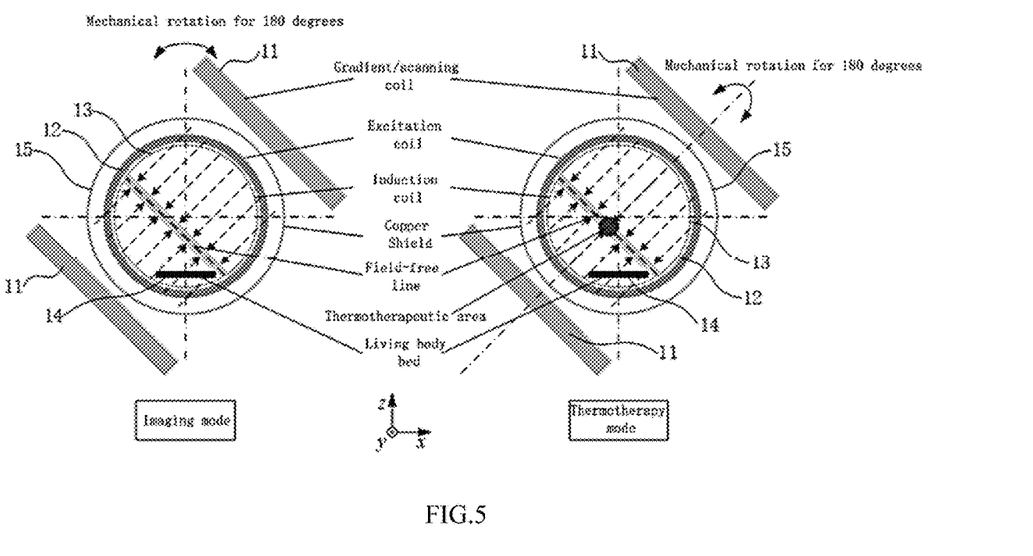
FIG. 5 is a schematic diagram illustrating the operation of the field-free line scanning tomographic image group based on magnetic nanoparticles and the field-free point positioning local quantitative thermotherapy based on magnetic nanoparticles in an embodiment of the present invention.

In embodiment 2, as shown in FIG. 2, a method for magnetic particle imaging and thermotherapy fusion based on field-free line inertial scanning, comprising the steps of:

Step 100: constructing a gradient magnetic field based on the long curved magnetic body pair and forming a field-free line;

In this embodiment, the current component in reverse direction is introduced into the long curved magnetic body pair 11 to construct a gradient magnetic field while forming a field-free line;

Step 200: controlling the field-free line to translationally rotate in a plane perpendicular to the axis of the cylindrical magnetic body, and performing tomographic scanning on a target living body on the living body bed to obtain electromagnetic induction signals; subsequently, preprocessing the electromagnetic induction signals to obtain a tomographic image group;

In this embodiment, as shown in FIG. 5, in the imaging mode, through controlling the same-directional current component of the long curved magnetic body pair 11, the field-free line is enabled to translate and reciprocate along the central axis direction of the long curved magnetic body pair, and meanwhile, the long curved magnetic body pair is controlled to mechanically rotate in a reciprocating manner on the axis of the cylindrical magnetic body 12; therefore, the tomographic scanning on the target living body on the living body bed is realized, and electromagnetic induction signals are obtained;

The electromagnetic induction signals are preprocessed to form a tomographic image group; the preprocessing includes denoising and filtering amplification, and the tomographic image group includes a concentration distribution tomographic image of the magnetic nanoparticles, a temperature tomographic image of the distribution area, and an SAR (specific absorption rate) tomographic image of the distribution area;

Step 300: controlling a living body bed or a field-free line to move along the axis direction of the cylindrical magnetic body to a preset depth, and serial-layer-scanning the target living body on the living body bed to obtain a complete tomographic image group;

In this embodiment, the living body bed 14 is controlled to deliver the target living body 19 to a preset position in the cylindrical magnetic body, and the field-free line is moved along the axis direction of the cylindrical magnetic body 12 to a preset depth; meanwhile, the field-free line is controlled to perform translational rotation to form a serial-layer scanning, and the scanning surface is a plane formed by an axis perpendicular to the cylindrical magnetic body 12;

Step 400: classifying and fusing the complete tomographic image group to obtain a three-dimensional image group;

In this embodiment, the concentration distribution tomographic image of magnetic nanoparticles, the temperature tomographic image of the distribution area, and the SAR (specific absorption rate) tomographic image of the distribution area are fused to obtain a three-dimensional image of the concentration of magnetic nanoparticles, a three-dimensional image of the temperature of the distribution area, and a three-dimensional image of the SAR (specific absorption rate) of the distribution area;

Step 500: determining a thermotherapeutic program according to the three-dimensional image group, wherein the thermotherapeutic program includes the areas to be treated, the sequence of areas to be treated, the duration of thermotherapy and the size of areas to be treated;

In this embodiment, based on the three-dimensional image group, the areas to be treated, the sequence of areas to be treated, the duration of thermotherapy and the size of areas to be treated are determined through human or machine image recognition;

Step 600: constructing a gradient magnetic field based on the long curved magnetic body pair and forming a field-free line;

In this embodiment, the current component in reverse direction is introduced into the long curved magnetic body pair 11 to construct a gradient magnetic field while forming a field-free line;

Step 700: controlling the field-free line to rotate around the area to be treated and controlling the cylindrical magnetic body to generate a radio frequency magnetic field according to the thermotherapeutic program, thereby performing thermotherapy on the area to be treated;

In this embodiment, as shown in FIG. 5, in the thermotherapy mode, controlling the field-free line to rotate around the area to be treated, comprising:

Controlling the current of the long curved magnetic body pair, translating the long curved magnetic body pair to a preset position on a plane perpendicular to the axis of the cylindrical magnetic body, and controlling the long curved magnetic body pair to mechanically rotate around the axis of the cylindrical magnetic body to a specified angle, thereby enabling the center point of the field-free line, namely, the projection position of the area to be treated, to stay on the plane perpendicular to the axis of the cylindrical magnetic body;

Subsequently, controlling the living body bed by the control device, and delivering the area of the target living body to be treated to the plane formed by the central axis of the long curved magnetic body pair, or controlling the direct current component of the cylindrical magnetic body, and moving the field-free line along the axis direction of the cylindrical magnetic body to the area to be treated;

Finally, controlling the long curved magnetic body pair to mechanically rotate in a reciprocating manner around the central axis of the long curved magnetic body pair;

Additionally, a copper shield in FIG. 5 is used to eliminate the interference of the iron wire material outside the excitation coil or the induction coil on the apparatus for magnetic particle imaging and thermotherapy fusion based on field-free line inertial scanning;

Step 800: repeatedly switching between the imaging mode and the thermotherapy mode until the thermotherapeutic program is completed, wherein the imaging mode includes steps 100, 200 and 300, and the thermotherapy mode includes steps 600 and 700;

In this embodiment, the imaging mode and the thermotherapy mode are switched repeatedly to realize the recognition, analysis and thermotherapy of the areas to be treated until the thermotherapeutic program is completed; in this invention, preferably, during thermotherapy, the local temperature of all areas to be treated has reached 42° C. and is kept for 10 minutes.

During thermotherapy, to adjust the areas to be treated is to control the current component in reverse direction of the two long curved magnetic body pairs according to the size of the areas to be treated.

Figure 4:
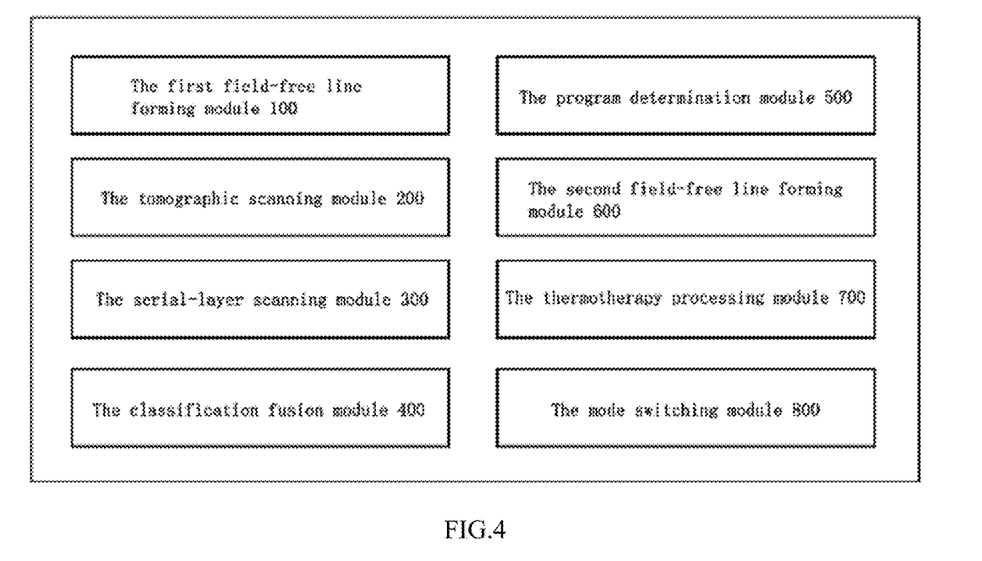
FIG. 4 is a schematic diagram illustrating a framework of the system for magnetic particle imaging and thermotherapy fusion based on field-free line inertial scanning in an embodiment of the present invention.

In embodiment 3 of the present invention, as shown in FIG. 4, a system for magnetic particle imaging and thermotherapy fusion based on field-free line inertial scanning comprises a first field-free line forming module 100, a tomographic scanning module 200, a serial-layer scanning module 300, a classification fusion module 400, a program determination module 500, a second field-free line forming module 600, a thermotherapy processing module 700 and a mode switching module 800.

The first field-free line forming module 100 is used to construct a gradient magnetic field based on the long curved magnetic body pair and form a field-free line.

The tomographic scanning module 200 is used to control the field-free line to translate and rotate in a plane perpendicular to the axis of the cylindrical magnetic body and perform tomographic scanning on the target living body on the living body bed to obtain electromagnetic induction signals. After the electromagnetic induction signals are preprocessed, a tomographic image group is obtained.

The serial-layer scanning module 300 is used to control the moving body bed or the field-free line to move along the axis direction of the cylindrical magnetic body to a preset depth and serial-layer-scan the target living body on the living body bed to obtain a complete tomographic image group.

The classification fusion module 400 is used to classify and fuse the complete tomographic image group to obtain a three-dimensional image group.

The program determination module 500 is used to determine a thermotherapeutic program according to the three-dimensional image group. The thermotherapeutic program includes the areas to be treated, the sequence of areas to be treated, the duration of thermotherapy and the size of areas to be treated.

The second field-free line forming module 600 is used to construct a gradient magnetic field based on the long curved magnetic body pair and form a field-free line.

The thermotherapy processing module 700 is used to control the field-free line to rotate around the area to be treated, control the cylindrical magnetic body to generate a radio frequency magnetic field, and perform thermotherapy on the area to be treated according to the thermotherapeutic program.

The mode switching module 800 is used to repeatedly switch between the imaging mode and the thermotherapy mode until the thermotherapeutic program is completed. The imaging mode includes the first field-free line forming module 100, the tomographic scanning module 200 and the serial-layer scanning module 300, and the thermotherapy mode includes the second field-free line forming module 600 and the thermotherapy processing module 700.

Those skilled in the art should clearly understand that, for the convenience and brevity of description, the specific operation and related description of the aforesaid system may refer to the corresponding process in the method of the present invention, and they are therefore briefly described herein.

It is worth mentioning that the apparatus/system for magnetic particle imaging and thermotherapy fusion based on field-free line inertial scanning in the embodiment of the present invention is merely illustrated by using the aforesaid functional modules. In practice, the aforesaid functions may be realized by different functional modules according to actual needs. Namely, the modules or steps in the embodiment of the present invention may be re-separated or combined. For instance, the modules in the aforesaid embodiment may be combined into one module or further separated into a plurality of submodules to achieve all or a part of the functions described above. The names of the modules and steps involved in the embodiment of the present invention are merely used to distinguish each module or step but not intended to limit the present invention.

In embodiment 4 of the present invention, an electronic device of the present invention comprises at least one processor and a memory connected to at least one processor, wherein the memory stores instructions that can be executed by the processor, and the instructions are executed by the processor to realize the method for magnetic particle imaging and thermotherapy fusion based on field-free line inertial scanning of the present invention.

In embodiment 5 of the present invention, a computer-readable storage medium is used to store computer instructions for being executed by a computer to realize the method for magnetic particle imaging and thermotherapy fusion based on field-free line inertial scanning of the present invention.

Those skilled in the art should clearly understand that, for the convenience and brevity of description, the specific operation and related description of the aforesaid electronic device and computer-readable storage medium may refer to the corresponding process in the method of the present invention, and they are therefore briefly described herein.

FIG. 6 is a schematic diagram illustrating a structure of a computer system for realizing the system, method and apparatus in embodiments of the present application. The server shown in FIG. 6 is merely an example, which does not place any restrictions on the function and scope of the embodiments of the present invention.

As shown in FIG. 6, the computer system includes a central processing unit (CPU) 601 capable of performing various processing according to the programs stored in the ROM (Read Only Memory) 602 or loaded into the RAM (Random Access Memory) 603 from a storage section 608. In RAM (Random Access Memory) 603, various programs and data required for system operation are also stored. CPU 601, ROM 602 and RAM 603 are connected to each other through a bus 604. The input/output (I/O) interface 605 is also connected to the bus 604.

The following components are connected to I/O interface 605: an input section 606 including a keyboard and a mouse, etc., an output section 607 including a cathode-ray tube, a liquid crystal display and a loudspeaker, etc., a storage section 608 including a hard disk, etc., and a communication section 609 of a network interface card including a local area network card and a modem, etc. The communication section 609 performs communication processing via a network such as the internet. An actuator 610 is also connected to the I/O interface 605. A removable medium 611, such as a magnetic disk, an optical disk, a magneto-optical disk and a semiconductor memory are mounted on the actuator 610, so that computer programs read therefrom are loaded into the storage section 608.

Specifically, according to the embodiments of the present invention, the process described in the flowchart can be implemented by a computer software program. For example, embodiments of the present invention include a computer program product, which includes a computer program loaded on a computer-readable medium, and the computer program includes program code for executing a method shown in the flowchart. In these embodiments, the computer program can be downloaded and installed from the network through the communication section 609, and/or installed from the removable medium 611. When the computer program is executed by the CPU (Central Processing Unit) 601, the aforesaid functions defined in the method of the present invention are executed. It is worth mentioning that, the computer-readable medium of the present invention may be a computer-readable signal medium, a computer-readable storage medium, or any combination of the aforesaid. The computer-readable storage medium includes but is not limited to, for example, an electrical, magnetic, optical, electromagnetic, infrared or semiconductor system, apparatus or device, or any combination of the aforesaid. More specifically, the computer-readable storage medium includes but is not limited to, an electrical connection with one or more wires, a portable computer disk, a hard disk, a RAM (Random Access Memory), a ROM (Read Only Memory), an erasable programmable read-only memory (EPROM or a flash memory), an optical fiber, a portable compact disk read only memory (CD-ROM), an optical storage device, a magnetic storage device, or any proper combination of the aforesaid. In the present invention, the computer-readable storage medium may be any tangible mediums containing or storing a program that may be used by or in combination with an instruction execution system, apparatus or device. In the present invention, a computer-readable signal medium may include data signals transmitted in baseband or as part of a carrier wave, in which the computer-readable program code is carried. The transmitted data signals may include various forms, including but not limited to electromagnetic signals, optical signals or any proper combination of the aforesaid. The computer-readable signal medium may also be any computer-readable mediums other than a computer-readable storage medium, which may send, propagate or transmit programs used by or in combination with an instruction execution system, apparatus or device. The program code contained in the computer readable medium can be transmitted by any suitable medium, including but not limited to wi-fi, wire, optical cable or any proper combination of the aforesaid.

The computer program code for performing operations of the present invention may be written in one or more programming languages or combinations thereof. The aforesaid programming languages include object-oriented programming languages, such as Java, Smalltalk and C++, and also include conventional procedural programming languages, such as C language or similar programming languages. The program code may be executed completely on a user computer, executed partially on a user computer, executed as an independent software package, executed partially on a remote computer or executed completely on a remote computer or server. A remote computer may be connected to a user computer via various networks, including a local area network or a wide area network, or may be connected to an external computer (e.g., connected via the Internet using an Internet service provider).

The flowcharts and block diagrams in the specification illustrate the possible architectures, functions and operations of the systems, methods and computer program products in embodiments of the present invention. In this regard, each block in a flowchart or block diagram may represent a module, program segment, or part of a code that contains one or more executable instructions for implementing a specified logical function. It should be noted that in some alternative implementations, the functions marked in the blocks may differ in sequence. For example, two consecutive blocks may actually be executed in parallel, or they may sometimes be executed in reverse sequence, depending on the functions involved. It should also be noted that each block in a block diagram and/or flowchart, and the combination of the blocks in a block diagram and/or flowchart, may be implemented with a dedicated hardware-based system that performs a specified function or operation, or may be implemented with a combination of dedicated hardware and computer instructions.

The terms "first" and "second" are used to distinguish similar objects instead of describing or indicating a specific order or sequence.

The term "including" or any other similar term is intended to cover non-exclusive inclusion. Therefore, a process, method, article or equipment/device including a series of elements not only includes those elements, but also includes other elements not explicitly listed, or further includes elements inherent in these processes, methods, articles or equipment/devices.

The above are merely preferred embodiments of the present invention, and the scope of the present invention is not limited to the embodiments described above. All technical solutions obtained under the idea of the present invention shall fall into the scope of the present invention. It should be noted that equivalent modifications and replacements may be made by those skilled in the art without departing from the principles of the present invention. Therefore, these improvements and modifications shall also fall into the scope of the present invention.

The invention claimed is:

1. An apparatus for magnetic particle imaging and thermotherapy fusion based on field-free line inertial scanning, comprising:
   a magnetic body group;
   an induction coil;
   a living body bed;
   a control device;
   a display device; and
   an image processing device,
   wherein the magnetic body group further comprises a long curved magnetic body pair and a cylindrical magnetic body,
   wherein the long curved magnetic body pair comprises two long curved magnetic bodies, each of the two long curved magnetic bodies comprises a first structural member, a second structural member and a third structural member,
   wherein the first structural member and the third structural member are U-shaped magnetic bodies,
   wherein the second structural member further comprises two symmetrical arc-shaped magnetic bodies prepared using a preset curvature,
   wherein the first structural member is parallel to the third structural member,
   wherein a plane where the second structural member is located is perpendicular to a plane where the first structural member is located,
   wherein two ends of the second structural member are respectively connected to open ends of the U-shaped magnetic bodies of the first structural member and the third structural member,
   wherein shapes of the long curved magnetic bodies are the same,
   wherein the long curved magnetic bodies are parallel to each other,
   wherein central axes of the long curved magnetic bodies are collinear,
   wherein closed ends of the first structural member or the third structural member of the long curved magnetic bodies of the long curved magnetic body pair are opposite of each other,
   wherein the cylindrical magnetic body is arranged in a space surrounded by the long curved magnetic body pair,
   wherein an axis of the cylindrical magnetic body is perpendicular to a central axis of the long curved magnetic body pair,
   wherein the long curved magnetic body pair is configured to simultaneously receive a current component in a same direction and a current component in a reverse direction for generating and translating a field-free line,
   wherein through changing the current component in the same direction, a biasing position of the field-free line is adjusted,
   wherein through changing the current component in the reverse direction, a gradient of a gradient magnetic field is adjusted,
   wherein the cylindrical magnetic body is configured to receive a direct current component and a radiofrequency current component,
   wherein the cylindrical magnetic body is configured to receive the direct current component for adjusting a depth of the field-free line in an axial direction of the cylindrical magnetic body,
   wherein the cylindrical magnetic body is configured to receive the radio frequency current component for induction heating of magnetic nanoparticles in a field-free region,
   wherein the control device is used to control current variation and mechanical rotation of the long curved magnetic body pair, current variation of the cylindrical magnetic body, and moving depth of the living body bed, according to a preset control command, thereby realizing translation, rotation and serial-layer scanning of the field-free line, realizing a scanning and imaging of a target living body and a positioning of the field-free line, and allowing thermotherapy to be performed on a preset area of the target living body.

2. The apparatus for magnetic particle imaging and thermotherapy fusion based on field-free line inertial scanning of claim 1, wherein when conducting positioning of the field-free line and performing thermotherapy on the preset area of the target living body by the control device, the induction coil is in an off state.

3. A method for magnetic particle imaging and thermotherapy fusion based on field-free line inertial scanning, using the apparatus for magnetic particle imaging and thermotherapy fusion based on field-free line inertial scanning of claim 2, comprising the steps of:

step 100: constructing the gradient magnetic field based on the long curved magnetic body pair and forming the field-free line;

step 200: controlling the field-free line to translationally rotate in a plane perpendicular to the axis of the cylindrical magnetic body, and performing tomographic scanning on a target living body on the living body bed to obtain electromagnetic induction signals; subsequently, preprocessing the electromagnetic induction signals to obtain a tomographic image group;

step 300: controlling the living body bed or the field-free line to move along the axial direction of the cylindrical magnetic body to a preset depth, and serial-layer-scanning the target living body on the living body bed to obtain a complete tomographic image group;

step 400: classifying and fusing the complete tomographic image group to obtain a three-dimensional image group;

step 500: determining a thermotherapeutic program according to the three-dimensional image group, wherein the thermotherapeutic program includes areas to be treated, a sequence of areas to be treated, a duration of thermotherapy and a size of areas to be treated;

step 600: constructing the gradient magnetic field based on the long curved magnetic body pair and forming the field-free line;

step 700: controlling the field-free line to rotate around the areas to be treated and controlling the cylindrical magnetic body to generate a radio frequency magnetic field according to the thermotherapeutic program, thereby performing thermotherapy on the areas to be treated;

step 800: repeatedly switching between an imaging mode and a thermotherapy mode until the thermotherapeutic program is completed, wherein the imaging mode dues includes steps 100, 200 and 300, and the thermotherapy mode includes steps 600 and 700.

4. The method for magnetic particle imaging and thermotherapy fusion based on field-free line inertial scanning of claim 3, wherein the tomographic image group further comprises a concentration distribution tomographic image of the magnetic nanoparticles, a temperature tomographic image of a distribution area, and a specific absorption rate tomographic image of the distribution area, wherein the three-dimensional image group further comprises a three-dimensional image of the concentration of magnetic nanoparticles, a three-dimensional image of the temperature of the distribution area, and a three-dimensional image of the specific absorption rate of the distribution area.

5. The method for magnetic particle imaging and thermotherapy fusion based on field-free line inertial scanning of claim 3, wherein controlling the field-free line to translate and rotate in a plane perpendicular to the axis of the cylindrical magnetic body, further comprises controlling the current component in the same direction of the long curved magnetic body pair, thereby enabling the field-free line to perform reciprocating translation along a central axis direction of the long curved magnetic body pair while controlling the long curved magnetic body pair to mechanically rotate in a reciprocating manner around the axis of the cylindrical magnetic body.

6. The method for magnetic particle imaging and thermotherapy fusion based on field-free line inertial scanning of claim 3, wherein controlling the living body bed or field-free line to move along the axis direction of the cylindrical magnetic body to a preset depth, and serial-layer-scanning the target living body on the living body bed, further comprises controlling the living body bed to deliver the target living body to a preset position in the cylindrical magnetic body, or controlling the current variation of the cylindrical magnetic body to make the field-free line to move along the axis direction of the cylindrical magnetic body to the preset depth; and further comprises controlling the field-free line to perform translational rotation to form a serial-layer scanning, and scanning surfaces of the serial-layer scanning are planes formed by an axis perpendicular to the cylindrical magnetic body.

7. The method for magnetic particle imaging and thermotherapy fusion based on field-free line inertial scanning of claim 3, wherein controlling the field-free line to rotate around the area to be treated, further comprises controlling the current variation of the long curved magnetic body pair, translating the long curved magnetic body pair to a preset position on a plane perpendicular to the axis of the cylindrical magnetic body, and controlling the long curved magnetic body pair to mechanically rotate around the axis of the cylindrical magnetic body to a specified angle, thereby enabling a center point of the field-free line, a projection position of the area to be treated, to stay on the plane perpendicular to the axis of the cylindrical magnetic body; subsequently, controlling the living body bed by the control device, and delivering the area of the target living body to be treated to the plane formed by the central axis of the long curved magnetic body pair, or controlling the direct current component of the cylindrical magnetic body, and moving the field-free line along the axis direction of the cylindrical magnetic body to the area to be treated; and further comprises controlling the long curved magnetic body pair to mechanically rotate in a reciprocating manner around the central axis of the long curved magnetic body pair.

8. The method for magnetic particle imaging and thermotherapy fusion based on field-free line inertial scanning of claim 3, wherein the size of areas to be treated may be adjusted by controlling the current component in reverse direction of the two long curved magnetic body pairs.

\* \* \* \* \*